United States Patent
Blau et al.

(10) Patent No.: US 9,517,107 B2
(45) Date of Patent: Dec. 13, 2016

(54) SURGICAL TARGETING SYSTEM AND METHOD

(75) Inventors: Arno Blau, Gundelfingen (DE); Bernd Simon, Kiel (DE); Michael Kohnen, Heitersheim (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 13/810,299

(22) PCT Filed: Jul. 16, 2010

(86) PCT No.: PCT/EP2010/060314
§ 371 (c)(1),
(2), (4) Date: Feb. 13, 2013

(87) PCT Pub. No.: WO2012/007054
PCT Pub. Date: Jan. 19, 2012

(65) Prior Publication Data
US 2013/0211386 A1    Aug. 15, 2013

(51) Int. Cl.
*A61B 19/00*    (2006.01)
*A61B 17/17*    (2006.01)

(52) U.S. Cl.
CPC ............ *A61B 19/26* (2013.01); *A61B 17/1703* (2013.01); *A61B 17/1717* (2013.01); *A61B 90/50* (2016.02);
(Continued)

(58) Field of Classification Search
CPC ............ A61B 17/1703; A61B 17/1717; A61B 2019/5238; A61B 19/54; A61B 19/26; A61B 90/50; A61B 2090/376; A61B 90/11; A61B 90/39
See application file for complete search history.

(56) References Cited

U.S. PATENT DOCUMENTS 5,122,141 A    6/1992    Simpson et al.
5,480,402 A    1/1996    Kim
(Continued)

FOREIGN PATENT DOCUMENTS

CN    1424673 A    6/2003
CN    1203435 C    5/2005
(Continued)

OTHER PUBLICATIONS

Ziv Yaniv, Member, IEEE, and Leo Joskowicz, Senior Member, IEEE, Precise Robot-Assisted Guide Positioning for Distal Locking of Intramedullary Nails, IEEE Transactions on Medical Imaging, vol. 24, No. 5, May 2005.*
(Continued)

*Primary Examiner* — Gary Jackson
*Assistant Examiner* — Scott T Luan
(74) *Attorney, Agent, or Firm* — Lerner, David, Littenberg, Krumholz & Mentlik, LLP

(57) ABSTRACT

A targeting system is used for positioning of a medical sub device with respect to a medical device. A reference body is reproducibly positioned with respect to a targeting device coupling section and reproducibly positioned with respect to a targeting unit. The targeting unit has a targeting direction and is adjustable with respect to the targeting device so that the targeting direction points toward a medical sub device receptacle of the medical device coupled to the targeting device coupling section. The imaging system is positionable with respect to the targeting device such that the imaging system is capable of imaging a single two-dimensional view of the reference body and the medical sub device receptacle. The evaluation unit generates position data of the single two-dimensional view and to determine from the position data a lateral distance between the targeting direction and a receiving direction of the medical sub device receptacle.

16 Claims, 7 Drawing Sheets

(52) U.S. Cl.
CPC ............... *A61B 90/11* (2016.02); *A61B 90/39* (2016.02); *A61B 2090/376* (2016.02)

(56) References Cited

U.S. PATENT DOCUMENTS

| | | | |
|---|---|---|---|
| 5,533,143 | A | 7/1996 | Takeo |
| 5,622,170 | A | 4/1997 | Schulz |
| 5,682,886 | A | 11/1997 | Delp et al. |
| 5,799,055 | A | 8/1998 | Peshkin et al. |
| 5,841,830 | A | 11/1998 | Barni et al. |
| 5,880,976 | A | 3/1999 | DiGioia, III et al. |
| 6,002,859 | A | 12/1999 | DiGioia, III et al. |
| 6,021,343 | A | 2/2000 | Foley et al. |
| 6,053,918 | A | 4/2000 | Spievack |
| 6,069,932 | A | 5/2000 | Peshkin et al. |
| 6,101,543 | A | 8/2000 | Alden et al. |
| 6,149,592 | A | 11/2000 | Yanof et al. |
| 6,198,794 | B1 | 3/2001 | Peshkin et al. |
| 6,205,411 | B1 | 3/2001 | DiGioia, III et al. |
| 6,226,548 | B1 | 5/2001 | Foley et al. |
| 6,285,902 | B1 | 9/2001 | Kienzle, III et al. |
| 6,341,231 | B1 | 1/2002 | Ferre et al. |
| 6,428,547 | B1 | 8/2002 | Vilsmeier et al. |
| 6,450,978 | B1 | 9/2002 | Brosseau et al. |
| 6,470,207 | B1 | 10/2002 | Simon et al. |
| 6,477,400 | B1 | 11/2002 | Barrick |
| 6,503,249 | B1 | 1/2003 | Krause |
| 6,510,241 | B1 | 1/2003 | Vaillant et al. |
| 6,535,756 | B1 | 3/2003 | Simon et al. |
| 6,674,883 | B1 | 1/2004 | Wei et al. |
| 6,697,664 | B2 | 2/2004 | Kienzle, III et al. |
| 6,701,174 | B1 | 3/2004 | Krause et al. |
| 6,711,432 | B1 | 3/2004 | Krause et al. |
| 6,718,194 | B2 | 4/2004 | Kienzle, III |
| 6,725,080 | B2 | 4/2004 | Melkent et al. |
| 6,747,646 | B2 | 6/2004 | Gueziec et al. |
| 6,810,280 | B2 | 10/2004 | Strobel |
| 6,856,826 | B2 | 2/2005 | Seeley et al. |
| 6,887,245 | B2 | 5/2005 | Kienzle, III et al. |
| 6,917,827 | B2 | 7/2005 | Kienzle, III |
| 6,922,581 | B2 | 7/2005 | Kienzle, III |
| 7,130,676 | B2 | 10/2006 | Barrick |
| 7,167,738 | B2 | 1/2007 | Schweikard et al. |
| 7,203,277 | B2 | 4/2007 | Birkenbach et al. |
| 7,235,076 | B2 | 6/2007 | Pacheco |
| RE40,176 | E | 3/2008 | Peshkin et al. |
| 7,392,076 | B2 | 6/2008 | Moctezuma de La Barrera |
| 7,427,200 | B2 | 9/2008 | Noble et al. |
| 7,427,272 | B2 | 9/2008 | Richard et al. |
| 7,567,834 | B2 | 7/2009 | Clayton et al. |
| 7,570,791 | B2 | 8/2009 | Frank et al. |
| 7,887,545 | B2 | 2/2011 | Fernandez et al. |
| 7,966,058 | B2 | 6/2011 | Xue et al. |
| 2001/0036245 | A1 | 11/2001 | Kienzle et al. |
| 2002/0188194 | A1 | 12/2002 | Cosman |
| 2004/0009459 | A1 | 1/2004 | Anderson et al. |
| 2004/0030245 | A1 | 2/2004 | Noble et al. |
| 2004/0039259 | A1 | 2/2004 | Krause et al. |
| 2004/0082849 | A1 | 4/2004 | Schweikard et al. |
| 2004/0097922 | A1 | 5/2004 | Mullaney |
| 2004/0171924 | A1 | 9/2004 | Mire et al. |
| 2004/0230199 | A1 | 11/2004 | Jansen et al. |
| 2004/0243148 | A1 | 12/2004 | Wasielewski |
| 2004/0263535 | A1 | 12/2004 | Birkenbach et al. |
| 2005/0021043 | A1 | 1/2005 | Jansen et al. |
| 2005/0027304 | A1 | 2/2005 | Leloup et al. |
| 2005/0065617 | A1 | 3/2005 | Moctezuma de la Barrera et al. |
| 2005/0075632 | A1 | 4/2005 | Russell et al. |
| 2005/0288679 | A1 | 12/2005 | Kienzle |
| 2006/0015030 | A1 | 1/2006 | Poulin et al. |
| 2006/0064106 | A1 | 3/2006 | Fernandez |
| 2006/0084867 | A1 | 4/2006 | Tremblay et al. |
| 2006/0098851 | A1 | 5/2006 | Shoham et al. |
| 2006/0173293 | A1 | 8/2006 | Marquart et al. |
| 2006/0241416 | A1 | 10/2006 | Marquart et al. |
| 2006/0281334 | A1 | 12/2006 | Shin et al. |
| 2007/0038059 | A1 | 2/2007 | Sheffer et al. |
| 2007/0038223 | A1 | 2/2007 | Marquart et al. |
| 2007/0161929 | A1 | 7/2007 | Maier |
| 2007/0270680 | A1 | 11/2007 | Sheffer et al. |
| 2008/0018643 | A1 | 1/2008 | Feilkas et al. |
| 2008/0051910 | A1 | 2/2008 | Kammerzell et al. |
| 2008/0075348 | A1 | 3/2008 | Rappaport et al. |
| 2008/0089566 | A1 | 4/2008 | Node-Langlois et al. |
| 2008/0119725 | A1 | 5/2008 | Lloyd |
| 2008/0243191 | A1 | 10/2008 | Tipirneni et al. |
| 2008/0269596 | A1 | 10/2008 | Revie et al. |
| 2008/0281334 | A1 | 11/2008 | Zheng et al. |
| 2008/0294265 | A1 | 11/2008 | Warkentine et al. |
| 2008/0319448 | A1 | 12/2008 | Lavallee et al. |
| 2009/0209851 | A1 | 8/2009 | Blau |
| 2009/0234217 | A1 | 9/2009 | Mire et al. |
| 2010/0030219 | A1 | 2/2010 | Lerner et al. |
| 2010/0104150 | A1 | 4/2010 | Saint Felix et al. |
| 2010/0168562 | A1 | 7/2010 | Zhao et al. |
| 2011/0019884 | A1 | 1/2011 | Blau |
| 2011/0184477 | A1 | 7/2011 | Dell'Oca et al. |
| 2011/0213379 | A1 | 9/2011 | Blau et al. |
| 2011/0313418 | A1 | 12/2011 | Nikonovas |
| 2013/0060146 | A1 | 3/2013 | Yang et al. |

FOREIGN PATENT DOCUMENTS

| | | |
|---|---|---|
| CN | 101069640 A | 11/2007 |
| DE | 102005062610 A1 | 6/2007 |
| DE | 102005062611 A1 | 6/2007 |
| DE | 102007008521 A1 | 8/2007 |
| DE | 102007008522 A1 | 8/2007 |
| EP | 0738502 A2 | 10/1996 |
| EP | 1491151 A1 | 12/2004 |
| EP | 1523950 A1 | 4/2005 |
| EP | 1859755 A2 | 11/2007 |
| EP | 1994914 A1 | 11/2008 |
| FR | 2895267 A1 | 6/2007 |
| GB | 2421187 A | 6/2006 |
| JP | 2000510730 A | 8/2000 |
| JP | 2005246059 A | 9/2005 |
| JP | 2008514296 A | 5/2008 |
| JP | 2010538753 A | 12/2010 |
| WO | 0209611 A2 | 2/2002 |
| WO | 03105659 A2 | 12/2003 |
| WO | 2004069040 A2 | 8/2004 |
| WO | 2005087125 A2 | 9/2005 |
| WO | 2007073733 A1 | 7/2007 |
| WO | 2007095917 A2 | 8/2007 |
| WO | 2007095918 A1 | 8/2007 |
| WO | 2007095919 A2 | 8/2007 |
| WO | 2009087214 A1 | 7/2009 |
| WO | 2012007054 A1 | 1/2012 |
| WO | 2012084056 A1 | 6/2012 |

OTHER PUBLICATIONS

Amir Herman et al., The International Journal of Medical Robotics and Computer Assisted Surgery, 5; 45-50, Dec. 29, 2008.
Communication from EP Application No. 10153136 dated Aug. 17, 2011.
International Search Report, PCT/EP2009/050210, dated Jun. 16, 2009.
Jagannathan et al., Neurosurg Focus 20, 2, E9, pp. 1-6, 2006.
Joskowicz et al., IEEE Transactions on Medical Imaging, IEEE Service Center, Piscataway NJ, US, vol. 24, No. 5, May 1, 2005, pp. 624-635.
PCT International Search Report PCT/EP2010/060314 dated Apr. 6, 2011.
Thomas C. Kienzle III et al., "An Integrated CAD-Robotics System for Total Knee Replacement Surgery", IEEE, 1993.
Hofstetter et al., "Computer-Assisted Fluoroscopy-Based Reduction of Femoral Fractures and Antetorsion Correction", Computer Aided Surgery 5:311-325 (2000).
International Search Report for PCT/EP2012/004102 dated Feb. 27, 2013.

(56) References Cited

OTHER PUBLICATIONS

Schulz et al., "Evidence Based Development of a Novel Lateral Fibula Plate (VariAx Fibula) Using a Real CT Bone Data Based Optimization Process During Device Development", The Open Orthopaedics Journal, 6:1-7 (2012).

* cited by examiner

SURGICAL TARGETING SYSTEM AND METHOD

CROSS-REFERENCE TO RELATED APPLICATION

The present application is a national phase entry under 35 U.S.C. §371 of International Application No. PCT/EP2010/060314 filed Jul. 16, 2010, published in English, incorporated herein by reference.

FIELD OF THE INVENTION

The present invention relates to a device and a method for a computer-assisted surgery, and in particular to a device and a method for computer-assisted surgery for placing a medical sub device with respect to a medical device by evaluating a single two-dimensional view of the situation.

BACKGROUND OF THE INVENTION

During surgery for inserting implants, it may be necessary to monitor the position of the inserted implant as well as to monitor a sub implant to be inserted and to be positioned with respect to the implant. A current method of inserting implant is typically accomplished by positioning the implant on the corresponding anatomical location and inserting a respective sub implant with the assistance of fluoroscopy. This, however, is an iterative process, which requires a repeated positioning of the sub implant with respect to the implant and taking a plurality of fluoroscopic images of the situation to monitor whether and in which direction the sub implant has to be repositioned with respect to the implant. For overcoming this iterative process problem, there are several proposals for providing a three-dimensional image of the situation in order to have a three-dimensional information allowing to conduct a positioning without repeated monitoring shots of a fluoroscopic imaging system. For this purpose, US 2010/0030219 A1 and US 2005/0027304 A1 describe an imaging, wherein the three-dimensional information is obtained by taking two different two-dimensional images from different viewing positions, i.e. angles, so as to generate a three-dimensional information. However, this requires taking two two-dimensional images, which, when using a standard C-arm fluoroscopic imaging system, requires a repositioning of the imaging system to obtain an image from a differing viewing position. This, however, may lead to a displacement of the imaged situation during repositioning, so that the resulting three-dimensional information may be erroneous.

SUMMARY OF THE INVENTION

Therefore, it is considered as an object of the present invention to provide a system and a method which overcomes the problem of displacements between two two-dimensional imaging shots, and/or to avoid the second two-dimensional imaging shot.

The object of the present invention is solved by a device and a method according to the subject-matter of the independent claims, wherein further embodiments are incorporated in the dependent claims.

It should be noted that the following described embodiments of the invention apply also for the device and the method as well as a computer program element and a computer readable medium.

According to an exemplary embodiment of the invention, there is provided a targeting system comprising a targeting device for positioning of a medical sub device with respect to a medical device, an imaging system and an evaluation unit, wherein the targeting device comprises a targeting device coupling section for uniquely coupling a medical device having a medical device coupling section and a medical sub device receptacle, a reference body, and a targeting unit, wherein the reference body is reproducibly positioned with respect to the targeting device coupling section and reproducibly positioned with respect to the targeting unit, wherein the targeting unit has a targeting direction and is adjustable with respect to the targeting device so that the targeting direction points toward a medical sub device receptacle of a medical device to be coupled to the targeting device coupling section, wherein the imaging system is positionable with respect to the targeting device such that the imaging system is capable of imaging a single two-dimensional view of the reference body and a medical sub device receptacle of a medical device to be coupled, wherein the evaluation unit is adapted to generate position data of the single two-dimensional view and to determine from the position data a lateral distance between the targeting direction and a receiving direction of a medical sub device receptacle of a medical device to be coupled.

Thus, a targeting system can be provided, which, by means of a reference body, is capable of providing unique information with respect to the spatial position thereof when taking a single two-dimensional image of the reference body, the medical sub device and the medical device. In particular, when the medical device has a certain displacement with respect to the reference body, for example in case the medical device or implant has a certain deformation, so that the targeting direction of the targeting system and the receiving direction of a receptacle for a medical sub device do not correspond to each other any longer. This may happen, for example, when using a targeting device in combination with, for example, an intramedullary nail, wherein the nail may be or is coupled to the targeting device. When inserting the intramedullary nail for example in the open marrow channel of the femur bone of the patient, the intramedullary nail, for example, may be bent owing to the marrow channel shape. Consequently the reference device does not fully represent the receptacle position of the nail for receiving, for example, a locking screw. The main deviation may be a deviation by bending, so that the receptacle is expected to be displaced either in a targeting direction, or displaced in a direction orthogonal to both, the targeting direction and the longitudinal extension of the nail, or displaced in a combination of the latter. When taking a single two-dimensional view of the reference body as well as the receptacle portion of the nail, which may be, for example, an opening for receiving a locking screw, owing to the unique view of the reference body and the known geometry of the nail, the displacement of the nail can be determined. This allows for a provision of a compensating means, which may be used for compensating the deviation, in particular, the deviation in a direction orthogonal to both of the targeting direction and the longitudinal extension of the nail.

The targeting direction is considered as a pointer starting substantially in the center of the targeting unit and having direction to a target, the targeting unit targets. The receiving direction is considered as a pointer starting substantially in the center of the receptacle and having direction from which direction for example a locking element approaches for being received into the receptacle. The targeting unit may be fixedly connected to the reference body, wherein the adjustability of the targeting unit is predefined with respect to the targeting device. As an alternative, the targeting unit may be adjustable with respect to the reference body, wherein the reference body is fixedly connected to the targeting device, wherein adjustability of the targeting unit is predefined with respect to the targeting device and reference body, respectively. The receptacle may serve as a locking receptacle or as receptacle for e.g. screws, bolts, nails and other elements.

A reference body may be, for example, a unique shape of a targeting section of the targeting system or targeting device, which, when imaged in any arbitrary direction, gives information on its spatial position, in particular with respect to the location and orientation thereof. However, the reference body may also be provided with particular fiducial markers in order to provide the unique image in a single two-dimensional view of the reference body. The same determination of the spatial position can be taken from the medical device, the geometry thereof is well-known. Thus, given that there are only two possible deviation directions, the geometry and possible position of the medical device may be determined with respect to the reference body. Thus, a lateral distance between the targeting direction and a receiving direction of the medical sub device receptacle of the medical device can be determined by evaluating the single two-dimensional view of the reference body and the medical sub device receptacle of a medical device. The targeting unit is adjustable, so that said lateral distance can be compensated by adjusting in order to bring the receiving direction and the targeting direction in correspondence to each other. Correspondence means that the targeting direction and the receiving direction are congruent to each other.

According to an exemplary embodiment of the invention, the reference body is removably coupled to the targeting unit.

Thus, a targeting device without reference body can be combined with a plug in reference body so as to form a targeting device according to the invention. In particular, the external targeting device may have a shaft and a coupling element, which may be brought into an engagement with the targeting unit of the targeting device. The external reference body may also have a separate targeting unit, which may for example be concentrically provided to the coupling shaft of the external reference body.

According to an exemplary embodiment of the invention the targeting unit is adjustable in a direction traverse to the targeting direction.

Thus, the targeting unit can be adjusted in order to meet the receiving direction of the medical sub device in order to bring the medical sub device and the medical device into engagement.

According to an exemplary embodiment of the invention the targeting unit is adjustable in a direction orthogonal to an extension of a medical device to be coupled to the targeting device coupling section.

Thus, in particular a one-dimensional bending in a direction orthogonal to an extension of a medical device to be coupled to the targeting device coupling section can be compensated in order to achieve corresponding targeting directions and receiving directions in order to allow bringing the medical sub device into engagement with the medical device.

According to an exemplary embodiment of the invention the reference body comprises a plurality of fiducial markers, wherein the plurality of fiducial markers is distributed so as to uniquely identify the position of the reference body when being imaged in any two-dimensional projection.

Thus, by providing a particular distribution of the fiducial markers being visible in the imaging, even if using a material for the targeting system which does not show a proper contrast in an imaging, the spatial position of the reference body may uniquely be determined. The fiducial markers may be distributed such that the reference body has a two-dimensional projection being unique with respect to the orientation of the reference body with respect to the projecting direction. The reference body may also be provided without fiducial markers, but with a geometry such that the reference body has a two-dimensional image being unique with respect to the orientation of the reference body with respect to the imaging direction. The latter can be established by using image recognition.

According to an exemplary embodiment of the invention there is provided the above described targeting system further comprising a medical device, wherein the medical device comprises a medical device coupling section which medical device coupling section uniquely fits the targeting device coupling section, and a medical sub device receptacle, wherein the medical sub device receptacle has a receiving direction being parallel to the targeting direction.

Thus, not only a targeting system with a targeting device, but also in combination with a medical device can be provided, wherein the coupling of the medical device to the targeting system may ensure that the possible degrees of freedom can be limited to only a bending of the medical device with respect to the targeting device. Thus, any further displacement or movement of the medical device with respect to the targeting device may be excluded.

According to an exemplary embodiment of the invention the medical device is an intramedullary nail, wherein the medical sub device receptacle is an opening for receiving a locking screw as a medical sub device.

Thus, the targeting system with the adjustable targeting unit is capable of compensating a bending of an intramedullary nail, in particular when being inserted into the marrow channel of the bone. In particular, when the bone channel is deformed in such a way, that the intramedullary nail does not exactly follow the form of the channel, the intramedullary nail may be bended, so that the targeting direction and the receiving direction do not correspond any longer. This, however, may be compensated by adjusting the targeting unit so that the targeting direction and the receiving direction may be brought into correspondence.

According to an exemplary embodiment of the invention the evaluation unit is adapted to indicate the measure of the required adjustment to compensate the lateral distance of the targeting direction and the receiving direction.

Thus, the surgeon may directly receive an instruction on the amount of the required adjustment in order to compensate the lateral distance between the targeting direction and the receiving direction.

According to an exemplary embodiment of the invention the targeting device comprises a drive being capable of an automatic readjustment to bring the targeting direction and the receiving direction into congruence based on the determined lateral distance between the targeting direction and the receiving direction.

Thus, the surgeon only has to monitor the automatic readjustment of the targeting direction with respect to the receiving direction, so that the surgeon can concentrate on the application of the sub implant with respect to the implant without having to take care on the correctly adjusted position of the targeting unit.

According to an exemplary embodiment of the invention the imaging system comprises a radiating source and a sensor, wherein the sensor being sensitive with respect to the radiating source, wherein the radiating source is substantially punctual, wherein the evaluation unit is adapted to determine the lateral distance of the targeting direction and the receiving direction by evaluating a size of the projected medical sub device receptacle with respect to a size of the reference body so as to distinguish two translational degrees of freedom.

Thus, the system may distinguish a bending component in a direction being orthogonal to both, the targeting direction and the longitudinal extension of the intramedullary nail, from a bending component in direction of the targeting direction.

According to an exemplary embodiment of the invention, there is provided a method for targeting a medical sub device to a medical device, wherein the method comprises providing a targeting device, the targeting device comprising a targeting device coupling section for uniquely coupling a medical device having a medical device coupling section and a medical sub device receptacle, a reference body, and a targeting unit, wherein the reference body is reproducibly positioned with respect to the targeting device coupling section and reproducibly positioned with respect to the targeting unit, wherein the targeting unit has a targeting direction and is adjustable with respect to the targeting device so that the targeting direction points toward a medical sub device receptacle of a medical device to be coupled to the targeting device coupling section; positioning the targeting device, being uniquely coupled to a medical device with respect to an imaging system such that the imaging system is capable of imaging a two-dimensional projection of the reference body and the medical sub device receptacle having a receiving direction; imaging a single two-dimensional view of the reference body and the medical sub device receptacle; evaluating the single two-dimensional view; and determining from the single two-dimensional view a lateral distance of the targeting direction and the receiving direction.

Thus, a method can be provided which corresponds to the above described targeting system.

According to an exemplary embodiment of the invention evaluating comprises detecting the reference body and the medical device by image processing.

Thus, in particular by using an image and/or object recognition, the spatial position of the reference body as well as the spatial position of the medical device may be determined, so that the lateral distance between the targeting direction and the receiving direction may be determined from the evaluated three-dimensional situation of the image processing and object recognition.

According to an exemplary embodiment of the invention, there is provided a method, further comprising indicating a measure of a required adjustment for compensating the lateral distance of the targeting direction and the receiving direction.

Thus, the surgeon does not have to take care on the required adjustment, but can use the indicated measure as a base for readjustment.

According to an exemplary embodiment of the invention, there is provided a method, further comprising controlling a drive so as to automatically readjust the targeting unit to bring the targeting direction and the receiving direction into congruence based on the determined lateral distance of the targeting direction and the receiving direction.

Thus, the surgeon can concentrate directly onto the application of the medical sub device with respect to the medical device without the need for manual adjustment or readjustment.

According to an exemplary embodiment of the invention evaluating comprises evaluating a size of the imaged receptacle with respect to a size of the reference body, and determining comprises determining the lateral distance of the targeting direction and the receiving direction so as to distinguish two translational degrees of freedom.

Thus, two different translational degrees of freedom, namely bending in a direction to the targeting direction and bending in a direction being orthogonal to both, the targeting direction and the longitudinal extension of the medical device can be distinguished so as to allow a correct adjustment of the targeting unit.

It should be noted that the above features may also be combined. The combination of the above features may also lead to synergetic effects, even if not explicitly described in detail. These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EXEMPLARY EMBODIMENTS

Figure 1:
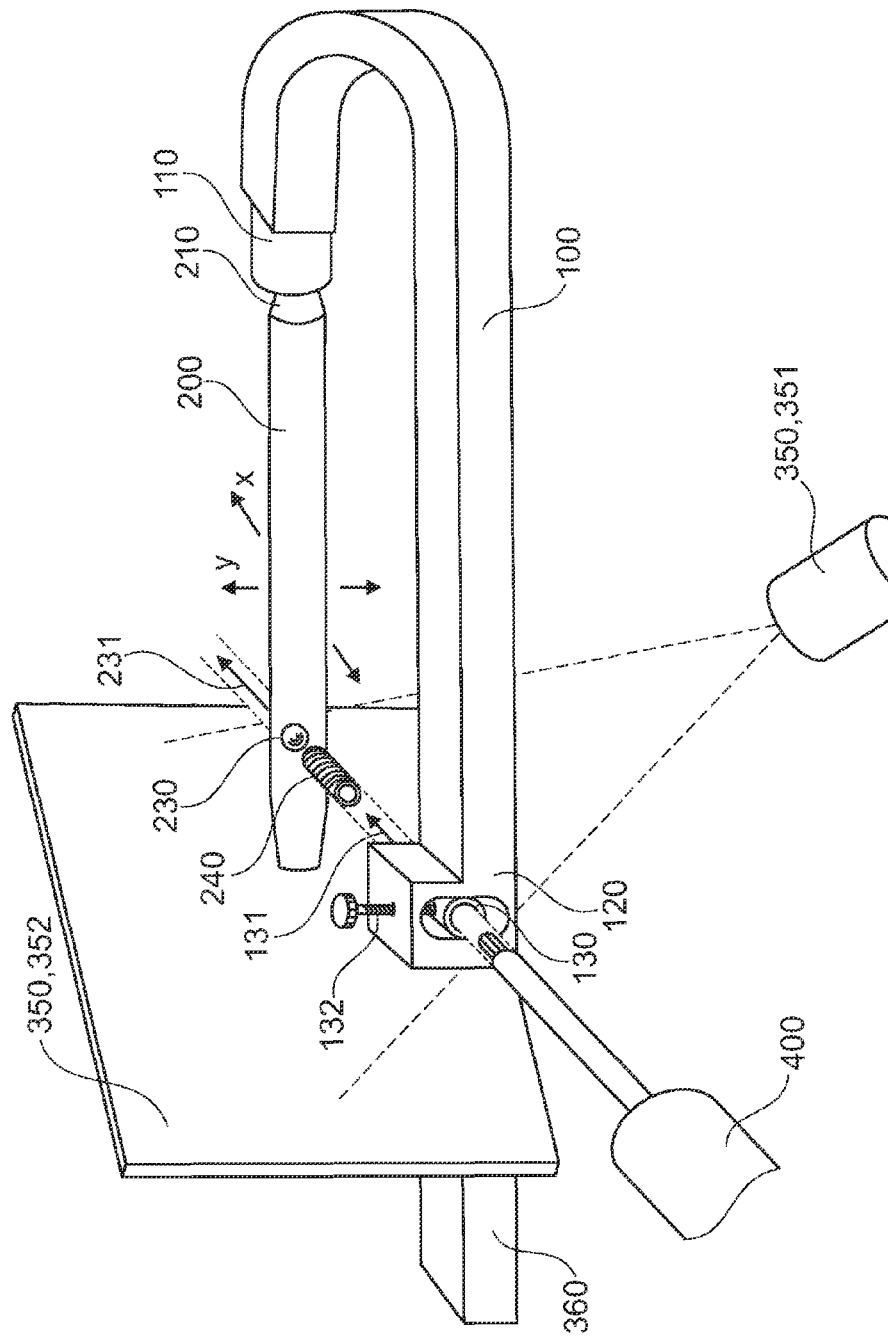
FIG. 1 illustrates a general overview over a targeting device, a medical device, and a medical sub device to be connected to the medical device according to an exemplary embodiment of the invention.

FIG. 1 illustrates an overview over a targeting device 100 having a medical device 200 coupled thereto. The medical device 200 comprises a medical device coupling section 210 which is coupled to a targeting device coupling section 110 of the targeting device 100. The targeting device further comprises a targeting unit 130, wherein the targeting unit is adjustably mounted to the targeting device 100. The targeting unit 130 has a reproducible position with respect to a reference body 120 being connected to the targeting device. The targeting unit 130 can be used for guiding a tool 400, wherein the tool 400 may be used to connect a medical sub device 240 to the medical device 200. The guiding direction as the targeting direction 131 corresponds to the mounting direction of the medical sub device 240. The targeting device is designed such that the guiding or targeting direction 131 directly points toward for example a receptacle 230 of the medical device. Thus, the targeting direction 131 and the receiving direction 231 are congruent to each other. However, in case the medical device 200 is introduced into the human body, for example into the marrow channel of a bone, the marrow channel may have some deformations, so that the medical device 200 in form of, for example, an intramedullary nail may be deformed. A deformation may be for example in form of a bending into the Y-direction or the X-direction. In this case, the medical device 200 is deformed by bending, so that the receptacle 230 is displaced with respect to the targeting device or the targeting unit. Consequently the targeting direction 131 does not correspond to the receiving direction 231 any longer. In the particular case shown in FIG. 1, a bending into the X-direction does not mandatorily lead to a lateral distance d between the targeting direction 131 and the receiving direction 231. Even if there is a certain minimum inclination of the receiving direction 231, this minor inclination mostly will remain irrelevant so that the medical sub device 240 can also be received in the receptacle 230 in case the medical device 200 is bended only into the X-direction. However, if the medical device 200 is bended into the Y-direction, there is a certain amount of lateral distance d between the targeting direction 131 and the receiving direction 231, as the receiving direction 231 is displaced into the Y-direction so that the tool 400 when being positioned in the targeting unit 130, is not capable of putting the medical sub device 240 into the receptacle 230 any longer. It should be noted that the targeting direction is considered as a pointer starting substantially in the centre of the targeting unit and having a direction to the target, to which the targeting unit targets. In the same way, the receiving direction is considered as a pointer starting substantially in the centre of the receptacle and having a direction from which direction a medical sub device approaches for being received into the receptacle.

The lateral distance d between the targeting direction 131 and the receiving direction 231 into the Y-direction may be compensated by adjusting the targeting unit 130 by an adjustment means 132, so that, by adjusting the targeting direction 131 also into the Y-direction, the targeting direction 131 and the receiving direction 231 can be brought into congruence, so that the tool 400, when being applied to the targeting unit 130, will be capable of joining the medical sub device 240 and the receptacle 230.

In the exemplary embodiment shown in FIG. 1, a displacement is only expected into the X-direction or the Y-direction or a combination thereof, wherein a torsion displacement, an elongation, or a displacement into the longitudinal extension of the medical device 200 can be neglected. Moreover, owing to the elasticity of the medical device 200, the main deformations are expected into the Y-direction and the X-direction. As the position of the targeting device and the targeting unit on the one hand and the general dimensions of the medical device 200 on the other hand are well-known. As only a bending of the medical device 200 into the Y-direction and into the X-direction is to be expected, a single two-dimensional shot by an imaging system 350 can be used to determine the lateral distance d between the targeting direction 131 and the receiving direction 231, in particular into the Y-direction. The imaging system 350 may comprise, for example, a radiation source 351 being capable of emitting radiation which is partially transmitted by the human tissue and absorbed by at least certain portions of the reference body 120 and the medical device 200. An image recorded by the sensor device 352 may give information on the relative position of the targeting device and the targeting unit with respect to the receptacle 230 of the medical device 200. Further, an evaluation unit 360 may be provided, which is capable of evaluating the sensed irradiation, so as to determine the image data, which image data can be used for determining the lateral distance between the targeting direction 131 and the receiving direction 231.

The reference body 120 has a unique and characteristic projection when being put into the radiation beam between the radiation source 351 and the radiation sensor 352. This unique projection can be achieved, for example, when designing the reference body in a particular outer shape which is visible when being imaged in the imaging system, or by providing a particular distribution of fiducial markers 121. In this case, the reference body as such may be designed as a body being transparent for the radiation of the imaging system, wherein only the fiducial markers 121 are radiation absorbing.

Figure 2:
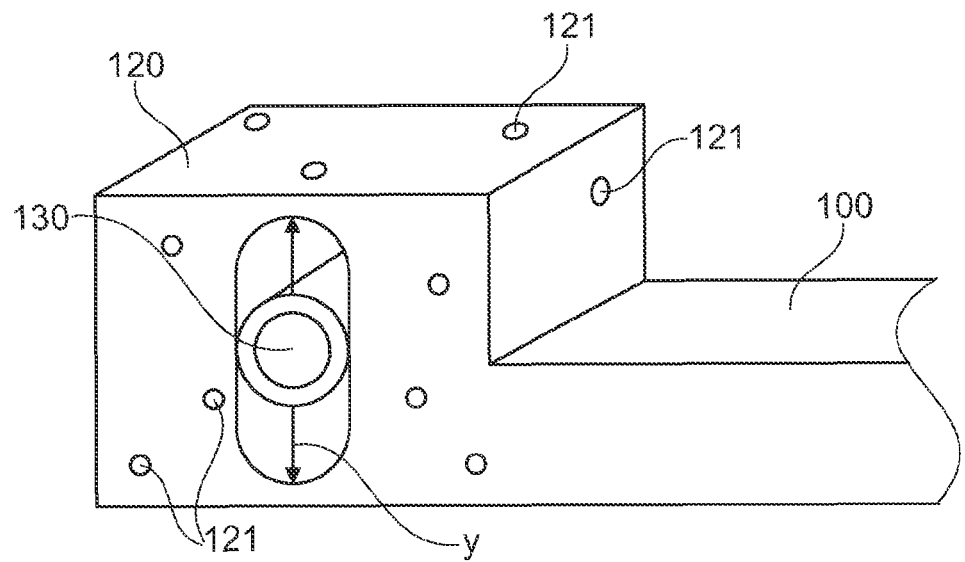
FIG. 2 illustrates a particular section of a targeting device with a reference body according to an exemplary embodiment of the invention.

FIG. 2 illustrates a particular section of the targeting device 100 with the reference body 120. The reference body 120 in FIG. 2 has a plurality of fiducial markers, so that the projection of the reference body including the fiducial markers 121 give a unique projection in any arbitrary projection direction. FIG. 2 illustrates that the targeting unit 130 is adjustable with respect to the reference body 120 and the fiducial markers into the Y-direction, so that a displacement or a lateral distance d between the targeting direction 131 and the receiving direction 231 can be brought into congruence. If taking a single two-dimensional image of the geometry of FIG. 2, together with the receptacle 230 of the medical device 200 (not shown) the surgeon can determine the lateral distance d between the targeting direction and the receiving direction, and afterwards can readjust the targeting unit 130 into the Y-direction unless the targeting direction 131 and the receiving direction 231 are brought into congruence.

Figure 3:
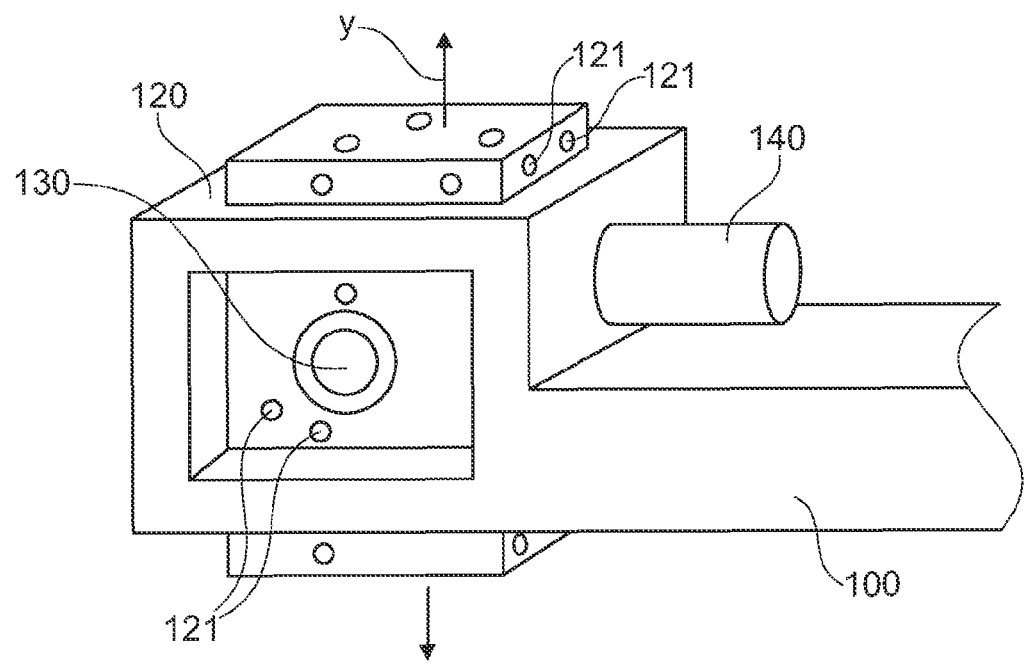
FIG. 3 illustrates a particular section of a targeting device with a reference body according to another exemplary embodiment of the invention.

FIG. 3 illustrates a further exemplary embodiment of the invention, wherein the targeting device 100 comprises a reference body 120, wherein the reference body 120 also comprises fiducial markers 121 for providing a unique projection in any arbitrary projection direction. The embodiment shown in FIG. 3 illustrates a reference body 120 which is movable or adjustable with respect to the targeting device 100 in order to adjust the targeting unit 130, which is fixedly mounted to the reference device. The adjusting of the targeting unit with respect to the targeting device 100, with the reference body fixed to the targeting unit (FIG. 3) and with the reference body fixed to the targeting device (FIG. 2), may be reproduceable, so that no further imaging is necessary when having analysed the single two-dimensional shot. Thus, if imaging the particular geometry of FIG. 3 together with the receptacle 230 of the medical device 200 (not shown), the surgeon may determine the lateral distance into the Y-direction in order to readjust the reference body 120 together with the targeting unit 130 in order to bring the targeting direction into congruence with the receiving direction. FIG. 3 further illustrates an additional drive device 140, which, when being coupled to the evaluating unit, may automatically adjust the targeting unit 130 with respect to the targeting device 100, based on the determined lateral distance d. As a matter of fact, the drive 140 may also be applied to the embodiment shown in FIG. 2.

Figure 4:
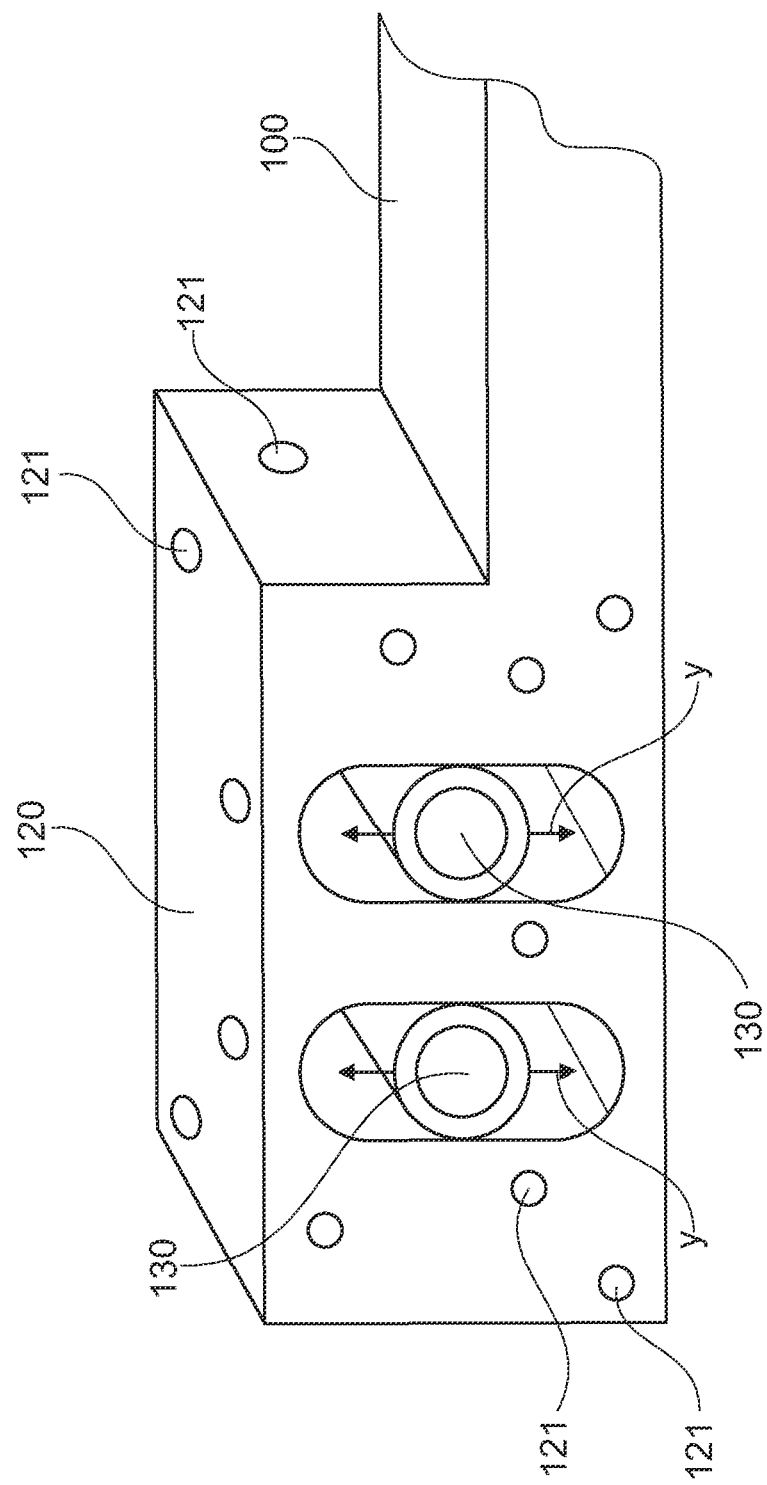
FIG. 4 illustrates a particular section of a targeting device with a reference body and a double targeting unit according to another exemplary embodiment of the invention.

FIG. 4 illustrates a particular section of a targeting device with a reference body and a double targeting unit 130. Each of the targeting units may be adjusted separately with respect to the reference body 120. However, the both targeting units 130 may also be coupled and then together synchronously adjusted with respect to the reference body 120. The targeting units may also be provided with separate reference bodies (not shown). In the latter case, each of the reference bodies may be fixedly connected with the respective targeting unit and separately movable with respect to the targeting device 100. This situation is similar to that shown in FIG. 3, but with two movable reference bodies. It should be noted that also more than two targeting units 130 may be provided, taking into account the required number of targeting units for respective medical sub-devices. Further, the double targeting unit 130 may also be provided in a single reference body 120, which single reference body is moveable with respect to the targeting device as shown in FIG. 3.

Figure 5:
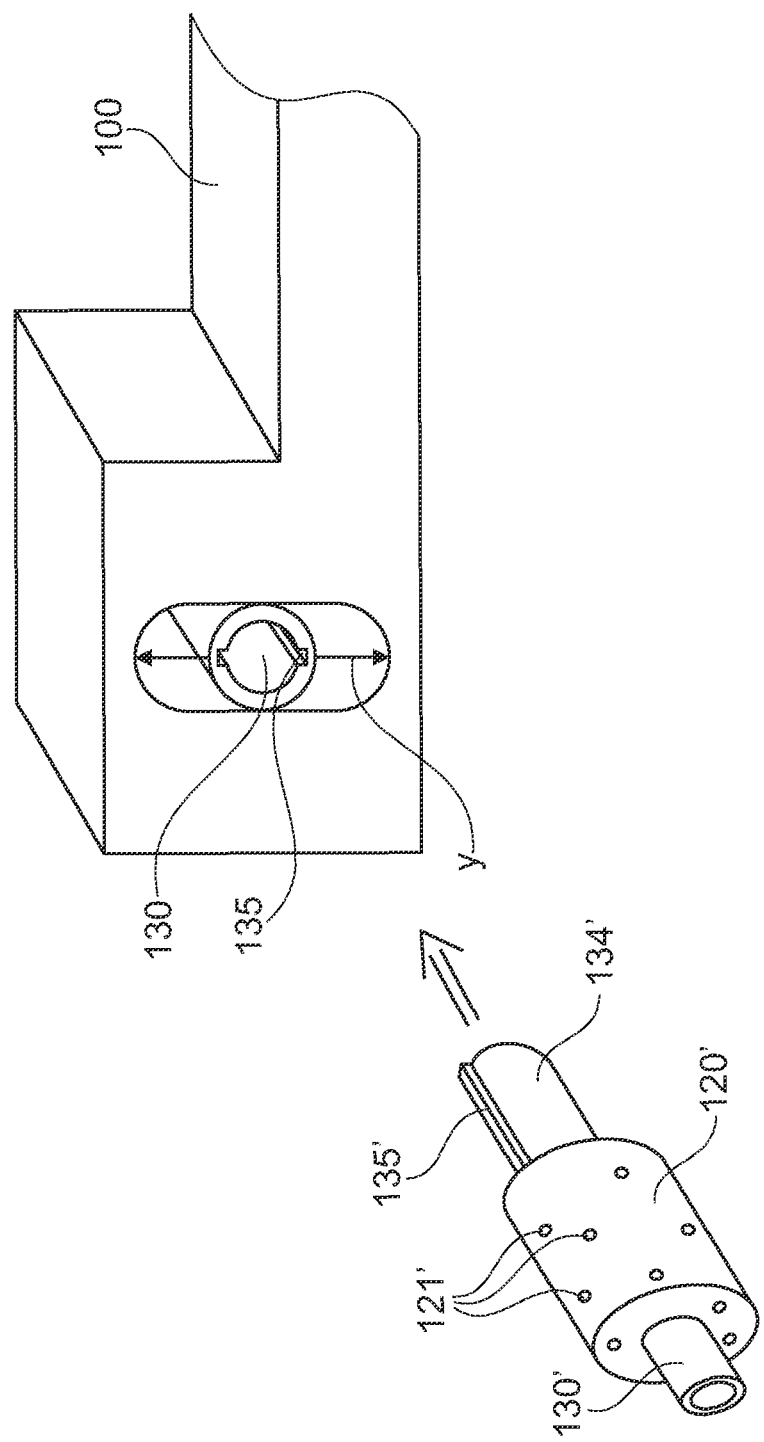
FIG. 5 illustrates a particular section of a targeting device with a plug in reference body according to another exemplary embodiment of the invention.

FIG. 5 illustrates a particular section of a targeting device with a plug in reference body. The targeting unit 130 may be provided with a coupling element 135 so as to couple an external targeting unit 130' and the plug in reference body 120'. Thus, it is not necessary to provide a reference body at the targeting device 100, but to use a common targeting device, and to plug in an external targeting unit 130' being fixedly connected to a reference body 130'. The external targeting unit has a shaft 134' matching the targeting unit 130, including the coupling element 135 at the targeting unit 130 and the coupling element 135' at the shaft 134'. The coupling elements 135 and 135' may be designed such that the targeting unit 130 may also be used without having set in the plug in reference body. For example, the targeting unit 130 on the targeting device may be provided with grooves as coupling element 135, allowing to put through and rotate a tool, wherein the coupling element 135' on the plug in reference device 120' may be provided as protruding tongues. The coupling elements 135 and 135' may also have a distribution or design to have a unique matching, e.g. different widths of the grooves and tongues or not equally distributed grooves and tongues. The reference body 120 may have a plurality of fiducial markers 121', but instead of or in addition may also have a unique shape allowing a unique identification in a projection of an image. In case of a plurality of targeting units 130 also a plurality of external targeting units 130' each having a reference body 120' may be provided.

Figure 6:
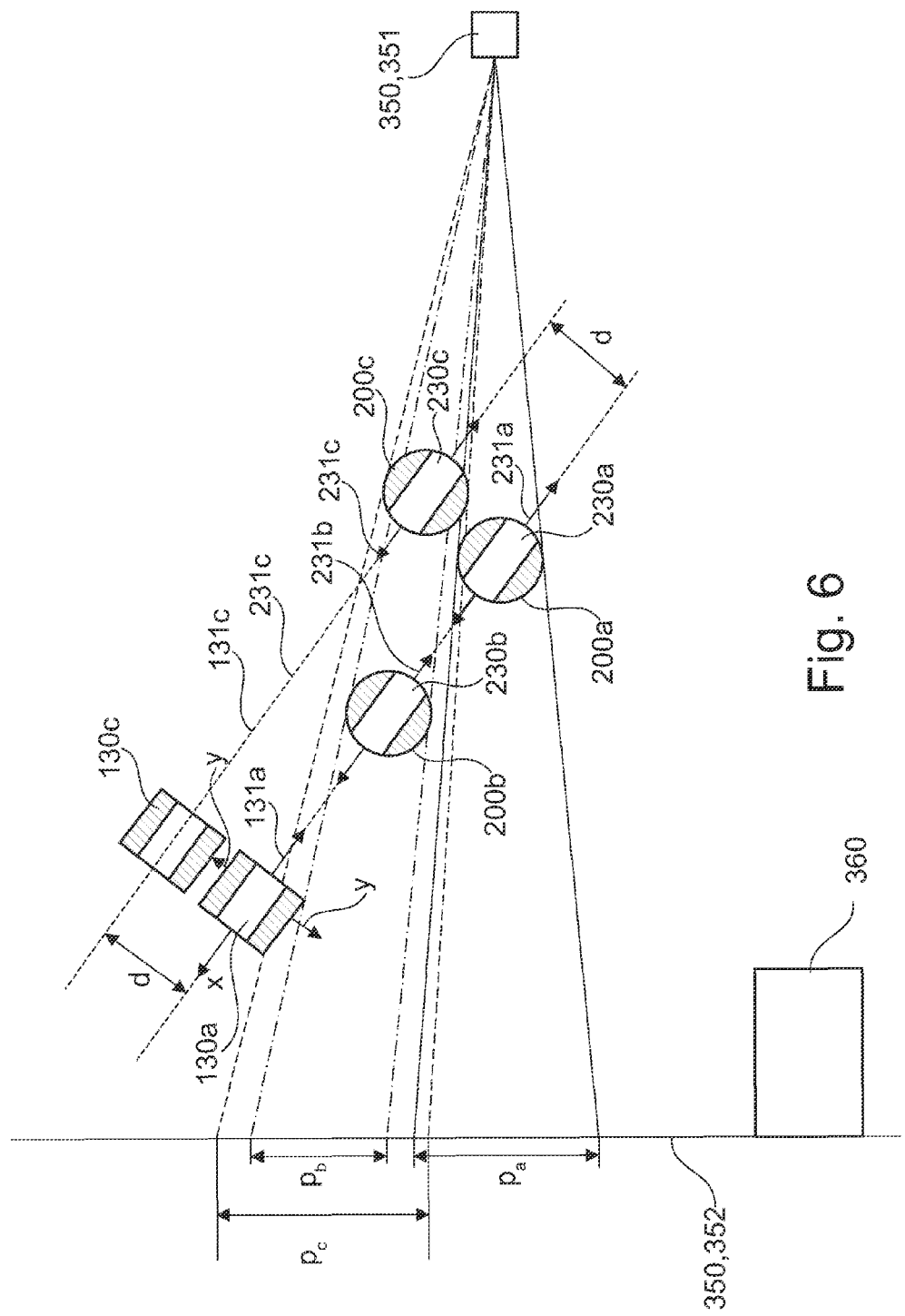
FIG. 6 illustrates a schematic overview over a projection scheme with respect to different positions of a medical device.

FIG. 6 illustrates a schematic overview over a sectional view of the targeting unit 130 and the medical device 200 including the receptacle 230. It should be noted that the remaining targeting device and particular adjustment elements are left out, as only the schematic relation between the targeting device 130 and the receptacle 230 should be illustrated. FIG. 6 illustrates three particular situations of the arrangement, wherein one situation is indexed with an "a", which is an original position of the targeting unit 130a and the medical device 200a, as well as the receptacle 230a. A further situation is illustrated with the index "b", which illustrates a displacement of the medical device 200b and the receptacle 230b into the X-direction, i.e. of the medical device towards the targeting unit 130, i.e. into the targeting direction 131a. A third situation is illustrated with an index "c", which illustrates a displacement of the medical device 200c and the receptacle 230c into the Y-direction, which corresponds to the lateral distance d. As the radiation source 351 of the imaging system 350 in the shown embodiment is an almost punctual radiation source, the system may distinguish between the displacement indexed with c and the displacement indexed with b by determining the dimension of the projected medical device 200c/200b, which leads to a projection $p_b$ and $p_c$. The size of the projection depends on the relative distance between the medical device and the punctual radiation source. As the projection $p_b$ and the projection $p_c$ are at the almost same position on the sensor 352, but the projection $p_b$ is smaller than the projection $p_c$, the system determines quantifies that the medical device 200c is closer to the radiation source 351 than the medical device 200b, so that the system distinguishes and determines from the position of the projection on the sensor 352 and the size of the projection that the displacement of the medical device 200c is into the Y-direction, and the displacement of the medical device 200b is into the X-direction. Thus, the system may distinguish between to generally different displacement of the medical device.

In case, the displacement is into the Y-direction, also the original receiving direction 231a is displaced by the lateral distance d so as to form a displaced receiving direction 231c. If the system and the evaluation unit 360 determine the displacement into the Y-direction of a lateral distance d, the surgeon may also displace the targeting unit 130a by the lateral distance d to arrive at the targeting unit 130c, so that the targeting direction 131c and the receiving direction 231c are brought into congruence. It should be noted that the displaced medical devices 200b and 200c only differ by the size of the projection $p_b$ and $p_c$, but have identical positions on the sensing device 352 of the imaging system 350.

Figure 7:
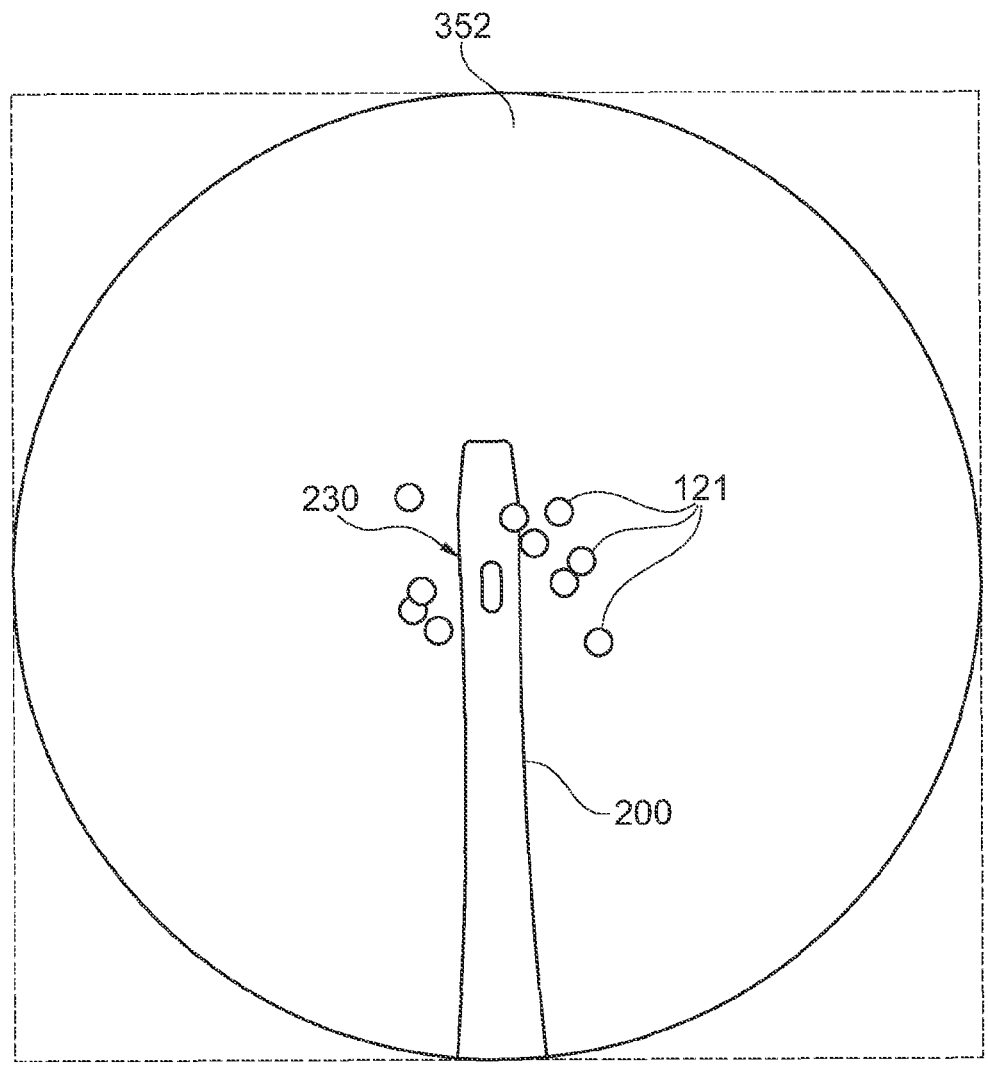
FIG. 7 illustrates a single two-dimensional view of a medical device in form of an intramedullary nail and fiducial markers of a reference body according to an exemplary embodiment of the invention.

FIG. 7 illustrates a single two-dimensional image of a medical device 200 and the fiducial markers 121 of the reference body. The relative positions of the fiducial markers to each other as well as the relative size of the fiducial markers 121 with respect to the medical device 200 and the receptacle 230 allow the determination of the lateral distance d (see FIG. 6), so that the surgeon may adjust or an automatic device may automatically adjust the targeting device (not shown in FIG. 7) so as to bring the targeting direction 131 into congruence with the receiving direction 231 (not shown in FIG. 7).

Figure 8:
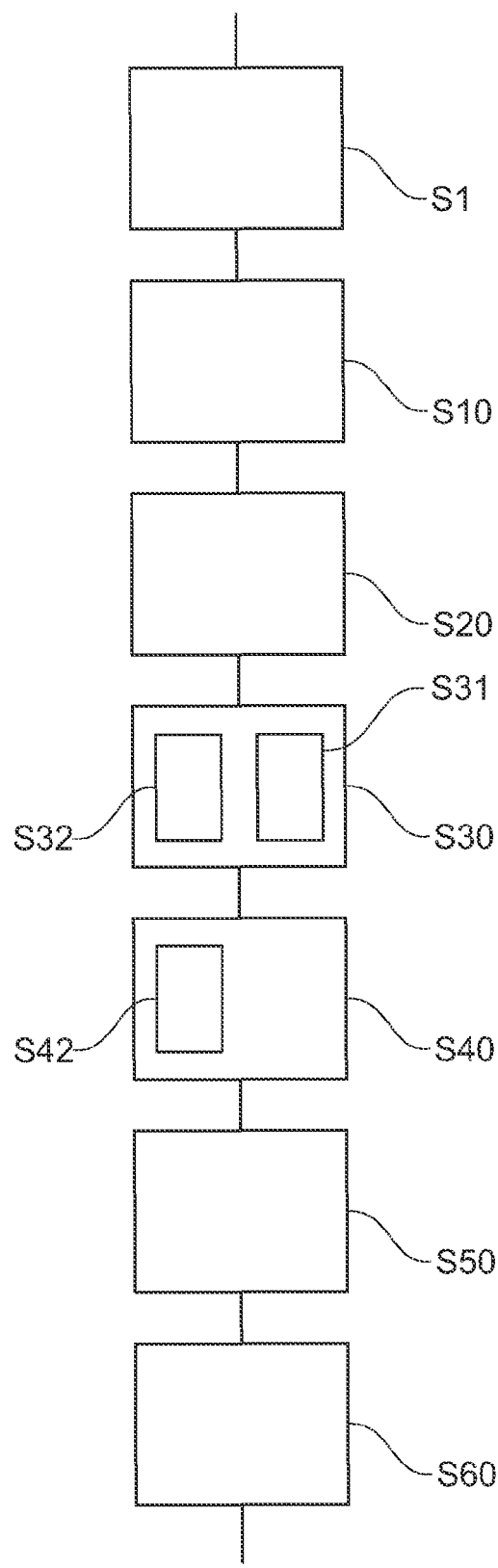
FIG. 8 illustrates a schematic overview over method according to an exemplary embodiment of the invention.

FIG. 8 illustrates a schematic overview over a method for targeting. The method comprises providing S1 a targeting device 100, the targeting device comprising a targeting device coupling section 110 for uniquely coupling a medical device 200 having a medical device coupling section 210 and a medical sub device receptacle 230, a reference body 120, and a targeting unit 130, wherein the reference body is reproducibly positioned with respect to the targeting device coupling section and reproducibly positioned with respect to the targeting unit, wherein the targeting unit has a targeting direction 131 and is adjustable with respect to the targeting device so that the targeting direction points toward a medical sub device receptacle 230 of a medical device to be coupled to the targeting device coupling section; positioning S10 the targeting device 130, being uniquely coupled to a medical device 200 with respect to an imaging system 350 such that the imaging system is capable of imaging a two-dimensional projection of the reference body 120 and the medical sub device receptacle 230 having a receiving direction 231; imaging S20 a single two-dimensional view of the reference body 120 and the medical sub device receptacle 230; evaluating S30 the single two-dimensional view; and determining S40 from the single two-dimensional view a lateral distance d of the targeting direction 131 and the receiving direction 231. As an option evaluating S30 comprises detecting S31 the reference body and the medical device by image processing. As a further option, the method further comprising indicating S50 a measure of a required adjustment for compensating the lateral distance d of the targeting direction 131 and the receiving direction 231. Further, the method may comprise controlling S60 a drive 140 so as to automatically readjust the targeting unit to bring the targeting direction 131 and the receiving direction 231 into congruence based on the determined lateral distance d of the targeting direction and the receiving direction. In addition, the evaluating S30 comprises evaluating a size S32 of the imaged receptacle 231 with respect to a size of the reference body 120, and determining S40 comprises determining S42 the lateral distance d of the targeting direction and the receiving direction so as to distinguish two translational degrees of freedom.

In another exemplary embodiment of the present invention, a computer program or a computer program element is provided that is characterized by being adapted to execute the method steps of the method according to one of the preceding embodiments, on an appropriate system. The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention. Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

It has to be noted that exemplary embodiments of the invention are described with reference to different subject matters. In particular, some exemplary embodiments are described with reference to apparatus type claims whereas other exemplary embodiments are described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage.

The invention claimed is:
1. A targeting system comprising:
a targeting device for positioning of a medical sub device with respect to a medical device,
an imaging system, and
an evaluation unit,
wherein the targeting device comprises:
a targeting device coupling section for uniquely coupling a medical device having a medical device coupling section and a medical sub device receptacle,
a reference body, and
a targeting unit,
wherein the reference body is reproducibly positioned with respect to the targeting device coupling section and reproducibly positioned with respect to the targeting unit;
wherein the targeting unit has a targeting direction and is adjustable with respect to the targeting device so that the targeting direction points toward a medical sub device receptacle of a medical device to be coupled to the targeting device coupling section;
wherein the imaging system is positionable in a direction with respect to the targeting device such that the imaging system is capable of imaging a single two-dimensional view of the reference body and the medical sub device receptacle of the medical device to be coupled;
wherein the targeting direction is angularly inclined from a sub-implant receiving direction of the medical sub-device receptacle;
wherein the evaluation unit is adapted to generate data from the single two-dimensional view and to determine from the data (i) a displacement of the medical sub device receptacle in a receiving direction of the medical sub device receptacle in a receiving direction of the medical sub device, and (ii) a lateral distance (d) between the targeting direction and the receiving direction of the medical sub device receptacle of the medical device to be coupled; and
wherein the imaging system comprises a radiating source and a sensor, the sensor being sensitive with respect to the radiating source, wherein the radiating source is substantially punctual, wherein the evaluation unit is adapted to determine the lateral distance (d) of the targeting direction and the receiving direction by evaluating a size of the projected medical sub device receptacle with respect to a size of the reference body so as to distinguish two translational degrees of freedom.

2. The targeting system according to claim 1, wherein the targeting unit is adjustable in a direction traverse to the targeting direction.

3. The targeting system according to claim 2, wherein the targeting unit is adjustable in a direction orthogonal to an extension of a medical device to be coupled to the targeting device coupling section.

4. The targeting system according to claim 1, wherein the reference body comprises a plurality of fiducial markers, wherein the plurality of fiducial markers is distributed so as to uniquely identify the position of the reference body when being imaged in any two-dimensional projection.

5. The targeting system according to claim 1, further comprising
a medical device, the medical device comprising
a medical device coupling section which medical device coupling section uniquely fits the targeting device coupling section, and
a medical sub device receptacle,
wherein the medical sub device receptacle has a receiving direction being parallel to the targeting direction.

6. The targeting system according to claim 5, wherein the medical device is an intramedulary nail, wherein the medical sub device receptacle is an opening for receiving a locking screw as a medical sub device.

7. The targeting system according to claim 1, wherein the evaluation unit is adapted to indicate the measure of the required adjustment to compensate the lateral distance (d) of the targeting direction and the receiving direction.

8. The targeting system according to claim 1, wherein the targeting device comprises a drive being capable of an automatic readjustment to bring the targeting direction and the receiving direction into congruence based on the determined lateral distance (d) of the targeting direction and the receiving direction.

9. A method for targeting a medical sub device to a medical device, the method comprising:
providing a targeting device, the targeting device comprising a targeting device coupling section for uniquely coupling a medical device having a medical device coupling section and a medical sub device receptacle, a reference body, and a targeting unit, wherein the reference body is reproducibly positioned with respect to the targeting device coupling section and reproducibly positioned with respect to the targeting unit, wherein the targeting unit has a targeting direction and is adjustable with respect to the targeting device so that the targeting direction points toward a medical sub device receptacle of a medical device to be coupled to the targeting device coupling section;
positioning the targeting device, being uniquely coupled to a medical device, with respect to an imaging system such that the imaging system is capable of imaging a two-dimensional projection of the reference body and the medical sub device receptacle having a receiving direction;
imaging a single two-dimensional view of the reference body and the medical sub device receptacle with an imaging direction being inclined to a receiving direction of the medical sub device;
evaluating the single two-dimensional view;
determining from the single two-dimensional view (i) a displacement of the medical sub device receptacle in a receiving direction of the medical sub device receptacle, and (ii) a lateral distance (d) of the targeting direction and the receiving direction; and
wherein evaluating comprises evaluating a size of the imaged receptacle with respect to a size of the reference body, and determining comprises determining the lateral distance (d) of the targeting direction and the receiving direction so as to distinguish two translational degrees of freedom.

10. The method of claim 9, wherein evaluating comprises detecting the reference body and the medical device by image processing.

11. The method according to claim 9, further comprising indicating a measure of a required adjustment for compensating the lateral distance (d) of the targeting direction and the receiving direction.

12. The method according to claim 9, further comprising controlling a drive so as to automatically readjusting the targeting unit to bring the targeting direction and the receiving direction into congruence based on the determined lateral distance (d) of the targeting direction and the receiving direction.

13. A targeting system comprising:
a targeting device coupled to a coupling section of a bone nail, the targeting device having a targeting sleeve for positioning a bone screw with respect to a bone screw receiving bore in the bone nail, the targeting sleeve and the bone screw receiving bore having a central axis;
a reference body mounted on the coupling section of the bone nail or on the targeting device;
an imaging system for imaging a two-dimensional image of the bone nail, the reference body and the targeting sleeve;
an image evaluation unit for determining the relative location of the targeting sleeve and the bone screw receiving bore in the nail;
wherein the reference body is positioned in a known location with respect to the coupling section of the bone nail and the targeting device;
wherein the targeting sleeve extends in a bone screw targeting direction, the targeting sleeve adjustable only in an anterior-posterior (A-P) direction with respect to the bone nail, the bone screw targeting direction extends along the central axis of the bone screw receiving bore in the bone nail;
wherein the imaging system is positionable in multiple directions with respect to the targeting system, the imaging system producing a single image in a single direction with respect to the targeting system wherein the evaluation unit determines, using the reference body image from only the single two-dimensional image, the distance in the A-P direction between the central axis of the bone screw receiving bore in the bone nail and the targeting sleeve bore central axis, the multiple imaging directions are all angularly inclined to the direction of the bone screw receiving bore central axis; and
wherein the imaging system comprises a radiating source and a sensor, the sensor being sensitive with respect to the radiating source, wherein the radiating source is substantially punctual, wherein the evaluation unit is adapted to determine the lateral distance (d) of the targeting direction and the receiving direction by evaluating a size of the projected medical sub device receptacle with respect to a size of the reference body so as to distinguish two translational degrees of freedom.

14. The targeting system according to claim 13, wherein the evaluation unit indicates a measure of a required adjustment of the targeting sleeve in the A-P direction for compensating for a distance (d) between the central axis of the targeting sleeve and the bone screw receiving bore.

15. The targeting system according to claim 14, further comprising a drive coupled to the device so as to automatically readjust the targeting sleeve to bring the sleeve central axis into alignment with the bone screw receiving bore central axis based on the determined distance (d).

16. The method according to claim 14, wherein the evaluating unit evaluates a size of the imaged bone with respect to a size of the reference body.

* * * * *